United States Patent
Takayama et al.

(10) Patent No.: US 10,256,004 B2
(45) Date of Patent: Apr. 9, 2019

(54) PARTICLE-BEAM CONTROL ELECTROMAGNET AND IRRADIATION TREATMENT APPARATUS EQUIPPED THEREWITH

(71) Applicants: KABUSHIKI KAISHA TOSHIBA, Minato-Ku (JP); Toshiba Energy Systems & Solutions Corporation, Kawasaki-Shi (JP)

(72) Inventors: Shigeki Takayama, Yokohama (JP); Tomofumi Orikasa, Yokohama (JP); Yoshifumi Nagamoto, Yokohama (JP); Takeshi Yoshiyuki, Yokohama (JP); Takashi Yazawa, Ota (JP)

(73) Assignees: KABUSHIKI KAISHA TOSHIBA, Minato-ku (JP); Toshiba Energy Systems & Solutions Corporation, Kawasaki-shi (JP)

( * ) Notice: Subject to any disclaimer, the term of this patent is extended or adjusted under 35 U.S.C. 154(b) by 0 days.

(21) Appl. No.: 15/737,379

(22) PCT Filed: Jun. 17, 2016

(86) PCT No.: PCT/JP2016/068145
§ 371 (c)(1),
(2) Date: Dec. 18, 2017

(87) PCT Pub. No.: WO2016/204283
PCT Pub. Date: Dec. 22, 2016

(65) Prior Publication Data
US 2018/0166180 A1    Jun. 14, 2018

(30) Foreign Application Priority Data
Jun. 19, 2015 (JP) .................... 2015-124144

(51) Int. Cl.
G21K 1/093 (2006.01)
G21K 1/00 (2006.01)
A61N 5/10 (2006.01)

(52) U.S. Cl.
CPC ............... *G21K 1/093* (2013.01); *G21K 1/00* (2013.01); *A61N 5/107* (2013.01); *A61N 5/1081* (2013.01); *A61N 2005/1087* (2013.01)

(58) Field of Classification Search
CPC .. G21K 1/10; G21K 1/00; G21K 1/093; H01J 37/141; A61N 5/107; A61N 5/1081
See application file for complete search history.

(56) References Cited

U.S. PATENT DOCUMENTS

| | | | | |
|---|---|---|---|---|
| 3,336,526 A | * | 8/1967 | Weaver, Jr. ............. | H01F 6/008 324/310 |
| 4,806,766 A | * | 2/1989 | Chisholm ............... | H01J 37/14 250/311 |

(Continued)

FOREIGN PATENT DOCUMENTS

| JP | 05-198400 A | 8/1993 |
|---|---|---|
| JP | 06-53000 A | 2/1994 |

(Continued)

OTHER PUBLICATIONS

International Preliminary Report on Patentability and Written Opinion dated Dec. 19, 2017 in corresponding PCT/JP2016/068145 filed Jun. 17, 2016.

(Continued)

*Primary Examiner* — Nicole M Ippolito
*Assistant Examiner* — Sean M Luck
(74) *Attorney, Agent, or Firm* — Oblon, McClelland, Maier & Neustadt, L.L.P.

(57) ABSTRACT

A particle-beam control electromagnet capable of shortening a transportation path of a particle beam and an irradiation (Continued)

treatment apparatus which contributes to miniaturization and weight reduction of the rotating gantry supporting this control electromagnet are provided. The electromagnet includes a first superconducting coil group, a second superconducting coil group, and a vacuum vessel. The first superconducting coil group forms at least one of a bending magnetic field and a focus/defocus magnetic field. The second superconducting coil group is placed around the trajectory of the particle beam at the end of the first superconducting coil group and forms correction magnetic fields for correcting the trajectory of the particle beam. The vacuum vessel hermetically houses the first superconducting coil group, the second superconducting coil group, and a cooling medium, and insulates from the outside air.

7 Claims, 4 Drawing Sheets

(56) References Cited

U.S. PATENT DOCUMENTS

| | | | | |
|---|---|---|---|---|
| 9,928,988 B2* | 3/2018 | Buff | | H01J 37/08 |
| 2002/0074524 A1* | 6/2002 | Nakano | | B82Y 10/00 |
| | | | | 250/505.1 |
| 2003/0089859 A1* | 5/2003 | Adamec | | H01J 37/141 |
| | | | | 250/396 ML |
| 2005/0285597 A1* | 12/2005 | Maki | | G01R 33/3875 |
| | | | | 324/320 |
| 2009/0166554 A1* | 7/2009 | Radovanov | | H01J 27/08 |
| | | | | 250/424 |
| 2010/0155597 A1* | 6/2010 | Preikszas | | H01J 37/05 |
| | | | | 250/310 |
| 2011/0140641 A1* | 6/2011 | Won | | H01J 27/18 |
| | | | | 315/502 |
| 2011/0148297 A1* | 6/2011 | Yasuda | | B82Y 10/00 |
| | | | | 315/5.35 |
| 2013/0008187 A1* | 1/2013 | Kraus | | F17C 3/08 |
| | | | | 62/51.1 |
| 2013/0134322 A1* | 5/2013 | Yasuda | | B82Y 10/00 |
| | | | | 250/396 ML |
| 2013/0256552 A1* | 10/2013 | Glavish | | H01J 37/05 |
| | | | | 250/396 ML |
| 2014/0145090 A9* | 5/2014 | Jongen | | A61N 5/10 |
| | | | | 250/396 R |
| 2015/0311037 A1* | 10/2015 | Kabasawa | | H01J 37/3171 |
| | | | | 250/397 |

FOREIGN PATENT DOCUMENTS

| | | |
|---|---|---|
| JP | 06-132098 A | 5/1994 |
| JP | 08-288100 A | 11/1996 |
| JP | 2011-072717 A | 4/2011 |
| JP | 4937196 B2 | 5/2012 |

OTHER PUBLICATIONS

International Search Report dated Aug. 30, 2016 in PCT/JP2016/068145, filed on Jun. 17, 2016.

* cited by examiner ved state of the first superconducting coil group and the
PARTICLE-BEAM CONTROL ELECTROMAGNET AND IRRADIATION TREATMENT APPARATUS EQUIPPED THEREWITH

FIELD

Embodiments of the present invention relate to a particle-beam control electromagnet and an irradiation treatment apparatus equipped therewith.

BACKGROUND

In particle beam therapy, a patient's lesion tissue (cancer) is irradiated with a particle beam such as carbon ions, and this particle beam therapy technique attracts attention.

In the particle beam treatment technique, it is possible to kill only the lesion tissue with pinpoint accuracy without damaging normal tissues. Thus, the particle beam treatment technique is less burdensome on patients than surgery, medication therapy or the like, and it can be expected to accelerate social reintegration after treatment.

In the early irradiation treatment apparatus, the irradiation portion of a particle beam was fixed, and the fixation method, in which irradiation was possible only from one direction with respect to a target, was mainstream.

In recent years, for the purpose of providing a more effective treatment, a rotation method has been spotlighted. In the rotation method, the irradiation portion of a particle beam is rotated so as to give an optimum dose value and optimum dose distribution to the lesion tissue depending on the shape of the lesion tissue and the body depth.

CITATION LIST

Patent Literature

[PTL 1] Japanese Unexamined Patent Application Publication No. 2011-72717

SUMMARY

Technical Problem

In an irradiation treatment apparatus of the rotation method, it is required to highly accurately control rotation of the rotating gantry supporting the irradiation portion of a particle beam in order to accurately irradiate the lesion tissue.

Additionally, the trajectory of a particle beam is guided along the rotation axis from the outside of the rotating gantry, then the particle beam once exits from the rotation axis to the outer circumference side of the rotating gantry, and then the particle beam is guided toward the inside of the rotating gantry along the radial direction.

A transportation path for controlling such the trajectory of the particle beam is formed by sequentially placing a quadrupole electromagnet (focus/defocus electromagnet) for controlling focus/defocus of the beam, a bending electromagnet for bending the beam trajectory, a steering electromagnet for correcting the beam trajectory, and the like.

A rotating gantry supporting such a lengthy transportation path is inevitable to be large in size, and a large rotating gantry has a concern that controllability of rotation deteriorates and its irradiation precision of a particle beam is reduced.

In view of the above-described problem, an object of embodiments of the present invention is to provide a particle-beam control electromagnet capable of shortening a transportation path of a particle beam and to provide an irradiation treatment apparatus which contributes to miniaturization and weight reduction of the rotating gantry supporting this control electromagnet.

DESCRIPTION OF EMBODIMENT

Figure 1:
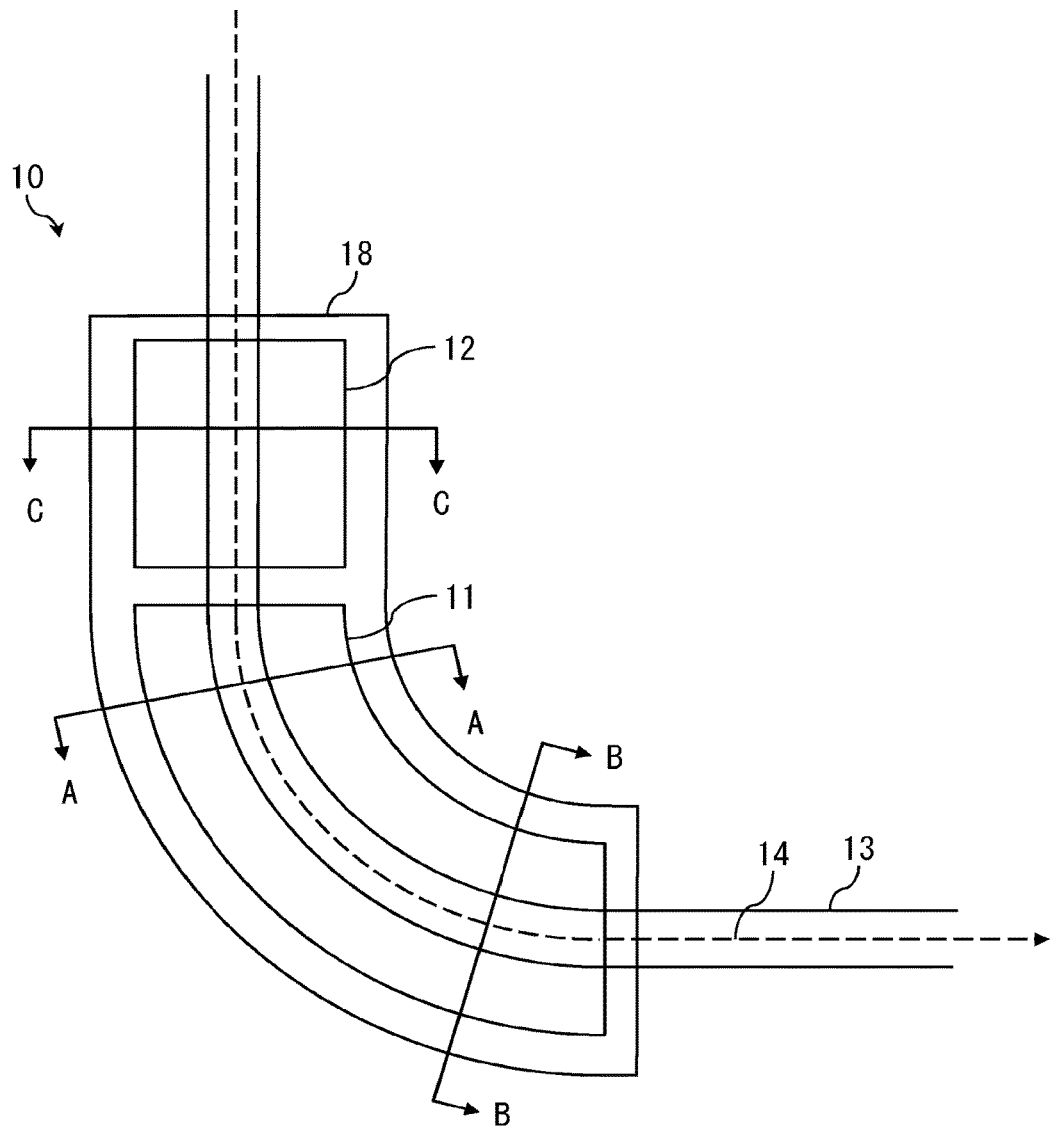
FIG. 1 is an outline view of a particle-beam control electromagnet according to one embodiment of the present invention.

Hereinafter, particle-beam control electromagnets according to each embodiment of the present invention will be described with reference to the accompanying drawings. In the drawings, the traveling direction of the particle beam is defined as the s-direction, and respective two directions being orthogonal to the s-direction and being orthogonal to each other are defined as the x-direction and the y-direction.

As shown in FIG. 1, the particle-beam control electromagnet 10 (hereinafter, abbreviated to the electromagnet 10) includes a first superconducting coil group 11, a second superconducting coil group 12, and a vacuum vessel 18. The first superconducting coil group 11 forms at least one of a bending magnetic field 15 (FIG. 2) and a focus/defocus magnetic field 16, the bending magnetic field 15 is for bending the traveling direction of a particle beam 14 passing inside a vacuum duct 13 and a focus/defocus magnetic field 16 is for controlling an outer diameter of the particle beam 14. The second superconducting coil group 12 is placed around the trajectory of the particle beam 14 at the end of the first superconducting coil group 11 and form correction magnetic fields 17 (17x and 17y shown in FIG. 3) for correcting the trajectory of the particle beam 14. The vacuum vessel 18 hermetically houses the first superconducting coil group 11, the second superconducting coil group 12 and a cooling medium (non-illustrated) so as to insulate from the outside air.

The vacuum duct 13 constitutes an ion generation source (non-illustrated), an accelerator (non-illustrated) and a transportation system (non-illustrated). The ion generation source is for generating the particle beam 14 such as carbon ions, negative pions, protons, helium ions, neon ions, silicon ions, or argon ions used for treatment. The accelerator such as a linear accelerator, a synchrotron, a cyclotron and an FFAG accelerator is for accelerating the particle beam 14. The transportation system is for transporting the particle beam 14 emitted from the accelerator to the target (patient 53 in FIG. 7).

Thus, the vacuum duct 13 is a sealed continuous space having a sufficient degree of vacuum for passing the particle beam 14 from the ion generation source to the target.

The cooling medium cools the superconducting coil to or below the critical temperature at which the superconductivity is developed. Examples of the cooling medium include a solid medium and a liquid medium. The solid medium thermally conducts a cold heat generated by a refrigerator to the superconducting coil. As the liquid medium a liquid nitrogen and a liquid helium are exemplified.

Figure 2:
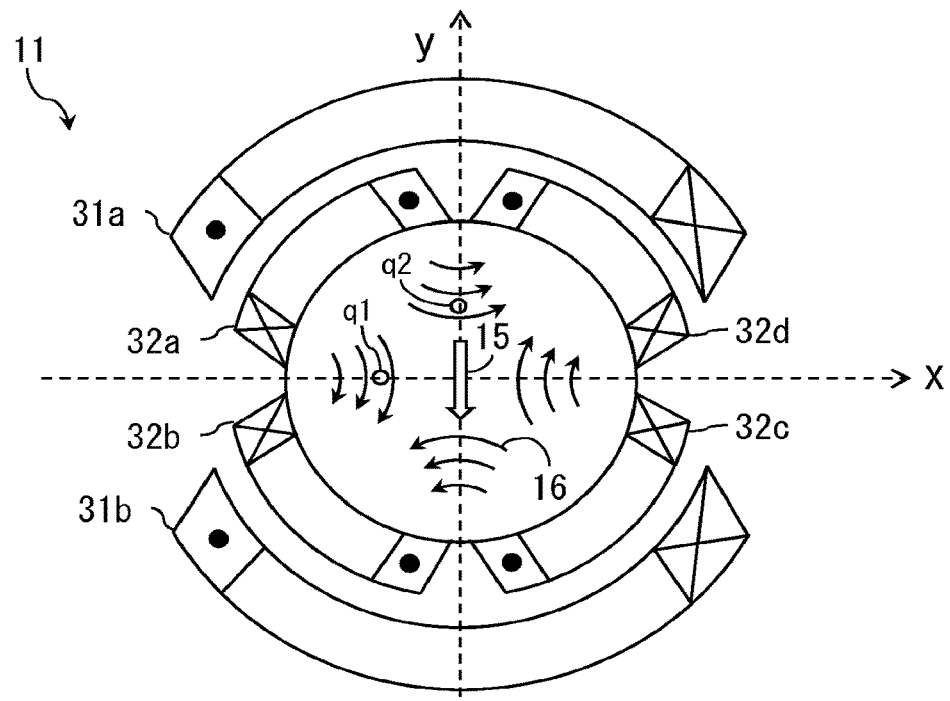
FIG. 2 is a cross-sectional view of a first superconducting coil group taken along the line A-A in FIG. 1.

FIG. 2 is a cross-sectional view of the first superconducting coil group 11 shown in FIG. 1 taken along the line A-A in FIG. 1.

The first superconducting coil group 11 is configured by the bending coils 31 (31*a* and 31*b*) and the focus/defocus coils 32 (32*a*, 32*b*, 32*c*, and 32*d*) are arranged to be coaxially stacked. The bending coils 31 (31*a* and 31*b*) is for forming the bending magnetic field 15 and the focus/defocus coils 32 (32*a*, 32*b*, 32*c*, and 32*d*) is for forming the focus/defocus magnetic field 16.

Although it is not illustrated in the drawing, on the cross-section B-B of the first superconducting coil group 11 (FIG. 1), focus/defocus coils 32 are further placed separately from the above-described focus/defocus coils 32 placed on the A-A cross-section. In the cross-section B-B (FIG. 1), the focus/defocus coils 32 are placed such that the focus/defocus coils 32 shown in FIG. 2 are rotated by 90° around the axis. In other words, the direction of the current flow is opposite but the structure is the same between the focus/defocus coils 32 placed on the cross-section A-A and the focus/defocus coils 32 placed on the cross-section B-B The bending coils 31 (31*a* and 31*b*) are composed of two excitation coils facing each other, and can bend the traveling direction of the particle beam passing therebetween by the action of the bending magnetic field 15 so as to make the beam trajectory into an arc shape. The particle beam passing through the bending coils 31 is made to travel straight in a tangential direction.

Although the bending coils 31 are exemplified by two excitation coils facing each other in the present embodiment, there are cases in which the bending coils 31 are composed of excitation coils of a number other than two.

The focus/defocus coils 32 (32*a*, 32*b*, 32*c*, and 32*d*) are composed of four excitation coils which are placed axially symmetrically, and form the focus/defocus magnetic field 16 indicated by the solid arrow in the inner gap in FIG. 2.

Although the focus/defocus coils 32 are exemplified by four excitation coils in the present embodiment, there are cases in which the focus/defocus coils 32 are composed of excitation coils of a number other than two. In particular, the focus/defocus coils 32 may be composed of even number (e.g., six) of excitation coils facing each other.

In the particle beam passing through the focus/defocus coils 32, the charged particles located at q1 on the x-axis are subjected to the Lorentz force in the center direction while the charged particles located at q2 on the y-axis are subjected to the outward Lorentz force. In other words, the focus/defocus coils 32 on the cross-section A-A converge the particle beam in the x-axis direction and diverges the particle beam in the y-axis direction. In the focus/defocus coils 32 of the cross-section B-B, the direction in which the beam converges and diverges is opposite such that the particle beam is converged in the y-axis direction and diverged in the x-axis direction.

The intensity of converging/diverging the beam can be controlled by intensity of direct currents applied to the respective focus/defocus coils 32.

By placing plural focus/defocus coils 32 with opposite polarities, and controlling the direct currents applied to the respective focus/defocus coils 32 as described above, it is possible to prevent divergence of the beam diameter of the particle beam and control the beam diameter to a desired size.

Although a description has been given of the case where the focus/defocus coils 32 are composed of two quadrupole coils 32 with opposite polarities in the present embodiment, the focus/defocus coils 32 may be composed of one, three, or more quadrupole coils 32.

Figure 3:
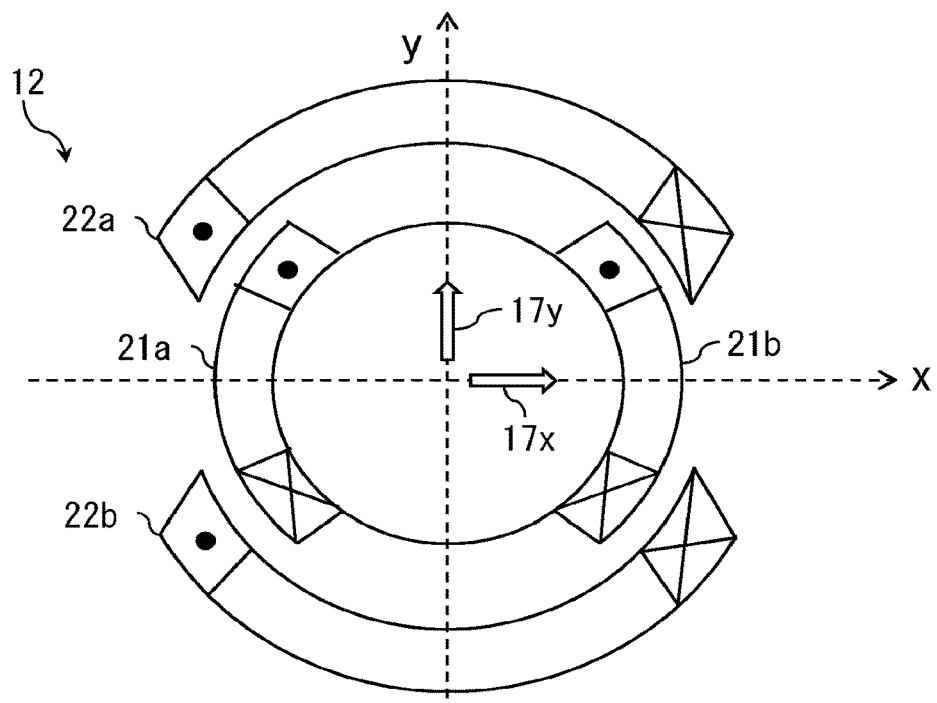
FIG. 3 is a cross-sectional view of a second superconducting coil group (steering magnets) taken along the line C-C in FIG. 1.

FIG. 3 is a cross-sectional view of the second superconducting coil group 12 (steering magnets) taken along the line C-C in FIG. 1.

The second superconducting coil group 12 includes first correction coils 21 (21*a* and 21*b*) and second correction coils 22 (22*a* and 22*b*). The first correction coils 21 form a first correction magnetic field 17*x* in the x-axis direction which is orthogonal to the traveling direction of the particle beam. The second correction coils 22 form a second correction magnetic field 17*y* in the y-axis direction which is orthogonal to the direction of the first correction magnetic field 17*x* and the traveling direction of the particle beam.

The first correction coils 21 have a configuration in which two excitation coils are arranged to face each other, similarly to the bending coils 31. The second correction coils 22 similarly have the configuration in which two excitation coils are arranged to face each other.

The role of the second superconducting coil group 12 is to correct the trajectory of the particle beam, which is caused by an error magnetic field generated by the installation error of the first superconducting coil group 11 or another error magnetic field generated by, e.g., individual differences among the first superconducting coil group 11 and/or other excitation coils.

The first correction magnetic field 17*x* formed by the first correction coils 21 and the second correction magnetic field 17*y* formed by the second correction coils 22 respectively correct the x-component and the y-component of the deviation of the trajectory of the particle beam.

Figure 4:
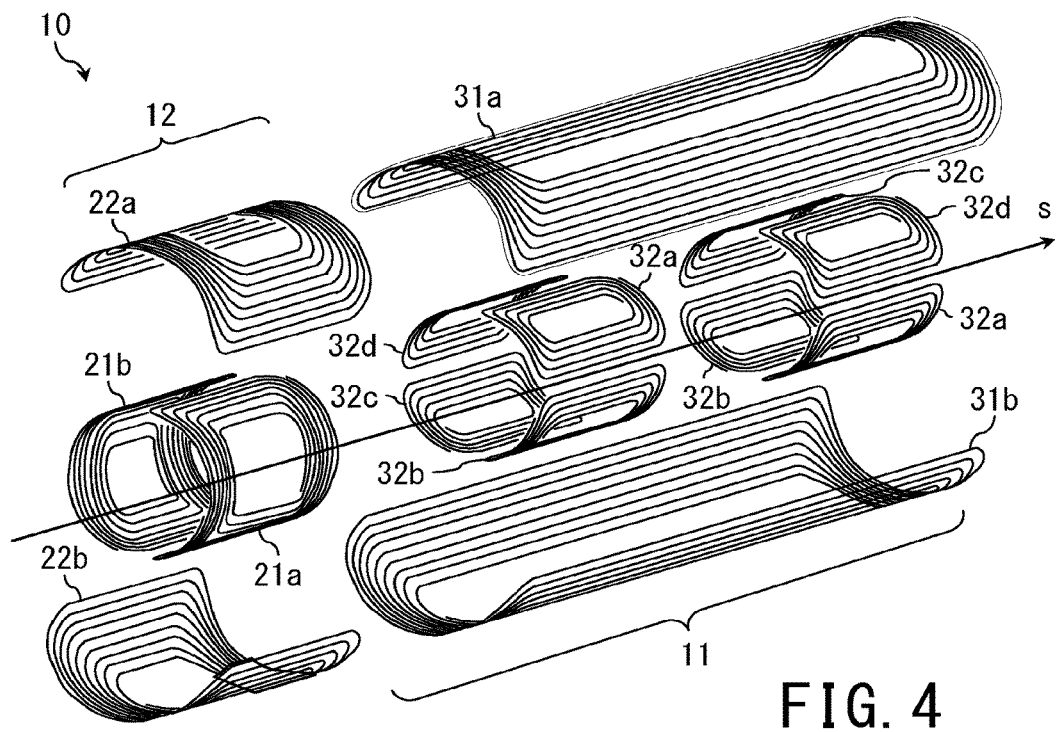
FIG. 4 is an exploded view illustrating a linearly developed state of the first superconducting coil group and the second superconducting coil group which constitute the particle-beam control electromagnet of one embodiment.

FIG. 4 is an exploded view illustrating a linearly developed state of the first superconducting coil group 11 and the second superconducting coil group 12 which constitute the electromagnet 10.

Actually, the first superconducting coil group 11 has a curved shape along the trajectory of the particle beam or is divided into plural coils placed in a curved shape along the trajectory of the particle beam.

As shown in FIG. 4, excitation coils constituting the first and second superconducting coil groups 11 and 12 are formed by winding a superconducting wire in an oval spiral shape, and the main surface of each of those excitation coils faces the outer peripheral surface of the vacuum duct 13 (FIG. 1).

In the electromagnet 10, the focus/defocus coils 32 (32*a*, 32*b*, 32*c*, and 32*d*) of the first superconducting coil group 11 and the first correction coils 21 (21*a* and 21*b*) of the second superconducting coil group 12 form a first layer which faces the vacuum duct 13 (FIG. 1). Further, the bending coils 31 (31*a* and 31*b*) and the second correction coils 22 (22*a* and 22*b*) form a second layer to be stacked on the first layer.

Figure 5:
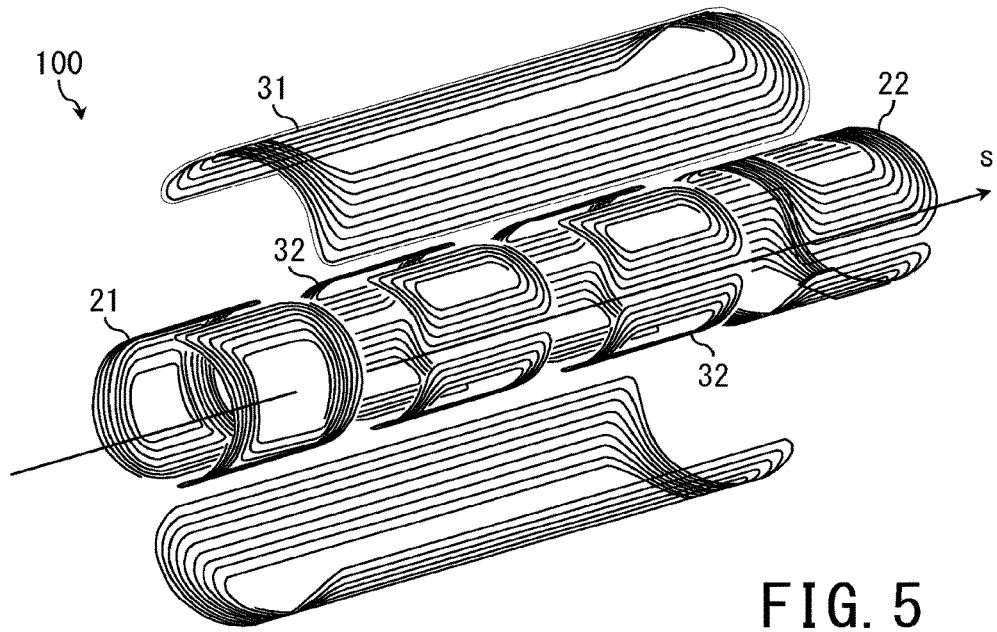
FIG. 5 is an exploded view illustrating a linearly developed state of the first superconducting coil group and the second superconducting coil group which constitute the particle-beam control electromagnet of another embodiment.

Although FIG. 4 illustrates one aspect in which the first correction coils 21 (21a and 21b) and the second correction coils 22 (22a and 22b) are arranged to be coaxially stacked. As shown in FIG. 5, in some cases, the first correction coils 21 and the second correction coils 22 are separately placed at both ends of the electromagnet 100.

Although a description has been given of the case where the first superconducting coil group 11 includes both the bending coils 31 and the focus/defocus coils 32 in the present embodiment. In some cases, the first superconducting coil group 11 includes either the bending coils 31 or the focus/defocus coils 32.

Although a description has been given of the case where the second superconducting coil group 12 includes both the first correction coils 21 and the second correction coils 22. In some cases, the second superconducting coil group 12 includes either the first correction coils 21 or the second correction coils 22.

Which one of FIG. 4, FIG. 5 and other aspects is selected is determined on the basis of viewpoints of reduction in length and performance which are required for the electromagnet 10 laid out in the vacuum duct 13.

Figure 6:
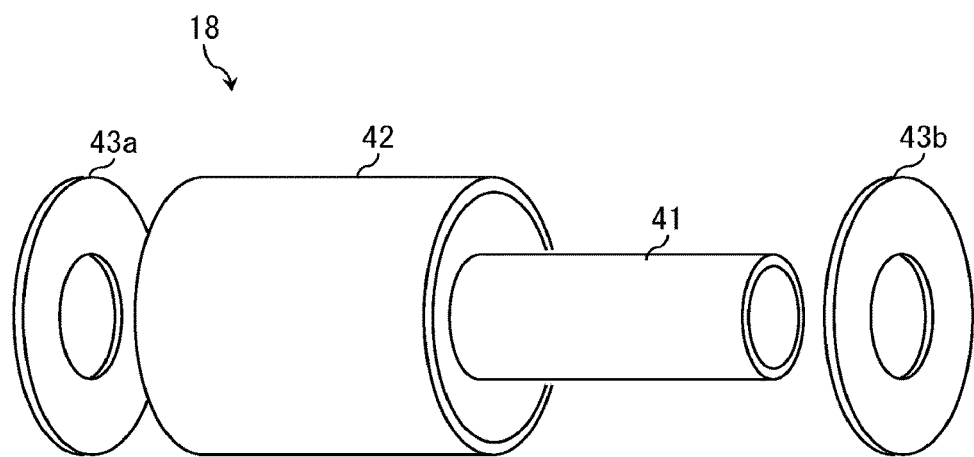
FIG. 6 is an exploded view illustrating a linearly developed state of a vacuum vessel.

FIG. 6 is an exploded view illustrating a linearly developed state of the vacuum vessel 18. Actually, the actual vacuum vessel 18 has a curvature as shown in FIG. 1.

The vacuum vessel 18 includes an inner cylinder 41, an outer cylinder 42 and end plates 43 (43a and 43b). The inner cylinder 41 is coaxially arranged with respect to the outer peripheral surface of the vacuum duct 13 (FIG. 1) in such a manner that there is an interval between the inner cylinder 41 and the outer peripheral surface of the vacuum duct 13. The outer cylinder 42 is coaxially arranged outside the inner cylinder 41. Each of the end plates 43 (43a and 43b) has a hole having the same diameter as the inner cylinder 41 at its center, and has the same outer diameter as that of the outer cylinder 42.

The respective peripheral edges of both ends of the inner cylinder 41 are brought into close contact with the peripheries of the holes of both end plates 43 (43a and 43b), and the respective peripheral edges of both ends of the outer cylinder 42 are brought into close contact with the outer peripheries of both end plates 43 (43a and 43b). As a result, an enclosed space is formed so as to be surrounded by the outer peripheral surface of the inner cylinder 41, the inner peripheral surface of the outer cylinder 42, and the surfaces of both end plates 43 (43a and 43b).

Each of the excitation coils constituting the first superconducting coil group 11 and the second superconducting coil group 12 is supported by a surface of at least one of the inner cylinder 41, the outer cylinder 42, and the end plates 43 (43a and 43b).

The enclosed space of the vacuum vessel 18 housing these excitation coils is filled with liquid refrigerant or held in a vacuum state.

When the enclosed space of the vacuum vessel 18 is kept in a vacuum state, the cold heat generated in the refrigerator conducts to the excitation coils thermally connected via a solid medium.

In this manner, the first superconducting coil group 11 and the second superconducting coil group 12 are cooled down to a temperature at which the superconductivity is developed by the cooling medium contained together in the enclosed space of the vacuum vessel 18.

Figure 7:
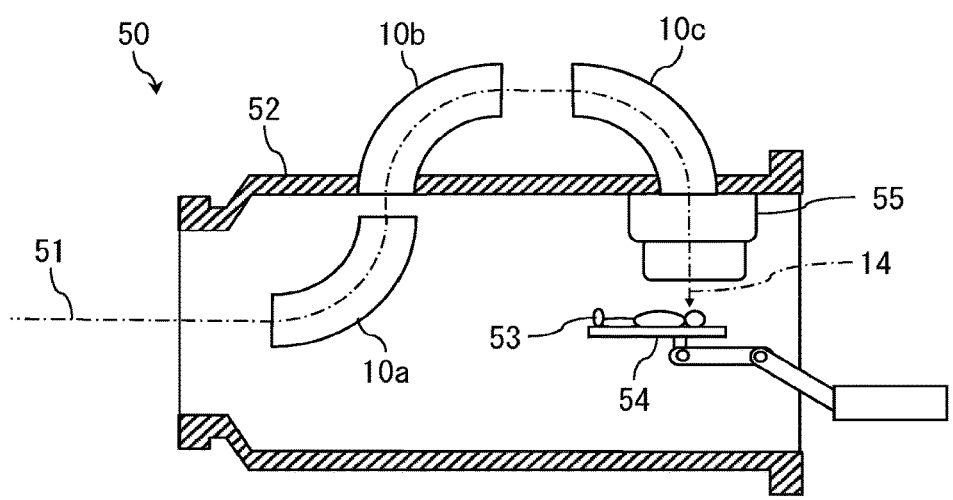
FIG. 7 is a cross-sectional view of an irradiation treatment apparatus according to one embodiment of the present invention.

FIG. 7 is a cross-sectional view of an irradiation treatment apparatus 50 according to one embodiment of the present invention.

The particle beam 14 decreases its speed by losing kinetic energy when passing through the body of the patient 53, and suddenly stops when falling to a certain speed by receiving a resistance which is approximately inversely proportional to the square of speed. In the vicinity of the stop point of the particle beam, high energy called Bragg peak is emitted.

The irradiation treatment apparatus 50 adjusts this Bragg peak to the lesion tissue of the patient 53 so as to kill the lesion tissue while suppressing damage on normal tissues.

The irradiation treatment apparatus 50 includes the electromagnets 10 (10a, 10b, and 10c), a rotating gantry 52, and a bed 54. The rotating gantry 52 supports the control electromagnets 10, rotates about the central axis 51, and irradiates the particle beam 14 in the direction orthogonal to the central axis 51. The bed 54 performs moving and positioning of the patient 53 placed thereon with respect to the particle beam 14 to be irradiated.

In an irradiation unit 55 provided inside the rotating gantry 52, a non-illustrated x-axis deflection scanning magnet for deflecting and scanning the particle beam 14 in the x-axis direction, a non-illustrated y-axis deflection scanning magnet for deflecting and scanning the particle beam 14 in the y-axis direction, and a non-illustrated range shifter for controlling penetration depth of the particle beam 14 in the s-axis direction are placed.

By placing the control electromagnets 10 (10a, 10b, and 10c) as shown in FIG. 7, it is possible to bend the trajectory of the particle beam 14 by 90° to guide along the rotation axis 51 of the gantry 52 and to irradiate the patient 53 with the particle beam 14 from an arbitrary direction orthogonal to the rotation axis 51.

Since each of the control electromagnets 10 is configured by housing a group of superconducting coils for generating a bending magnetic field, a focus/defocus magnetic field, and a correction magnetic field in one vacuum vessel, it is possible to reduce the size and weight of the rotating gantry supporting these coils.

According to the particle-beam control electromagnet of at least one embodiment described above, the transportation path of the particle beam can be shortened by accommodating the second superconducting coil group together with the first superconducting coil group in the vacuum vessel, in which the first superconducting coil group forming a bending magnetic field and/or a focus/defocus magnetic field and the second superconducting coil group forms a correction magnetic field for correcting the trajectory of the particle beam.

Some embodiments of the present invention have been described above, but these embodiments are given as mere examples and are not intended to limit the scope of the present invention. These embodiments can be carried out in various other modes, and can be variously omitted, replaced, changed, and combined within a range not departing from the gist of the present invention. These embodiments and modifications thereof are included in the scope and gist of the present invention, and are also included in the invention described in the claims and a range equivalent thereto.

The invention claimed is:

1. A particle-beam control electromagnet comprising:
    a first superconducting coil group configured to form a bending magnetic field and a focus/defocus magnetic field, the bending magnetic field is for bending a traveling direction of a particle beam passing through inside of a vacuum duct and the focus/defocus magnetic field is for controlling an outer diameter of the particle beam;

a second superconducting coil group configured to be placed around a trajectory of the particle beam at an end portion of the first superconducting coil group and form a correction magnetic field for correcting the trajectory of the particle beam; and a vacuum vessel configured to hermetically house the first superconducting coil group, the second superconducting coil group and a cooling medium to insulate from outside air, wherein the first superconducting coil group includes a first focus/defocus coil group and a second focus/defocus coil group arranged side by side along the trajectory of the particle beam, each focus/defocus coil group forming the focus/defocus magnetic field and including an even number of excitation coils placed axially symmetrically with respect to the trajectory of the particle beam, current flow in the excitation coils of the second focus/defocus coil group being opposite to current flow in the excitation coils of the first focus/defocus coil group.

2. The particle-beam control electromagnet according to claim 1, wherein the first superconducting coil group is configured by a bending coil and the focus/defocus coil groups are arranged coaxially stacked, the bending coil is for forming the bending magnetic field.

3. The particle-beam control electromagnet according to claim 2,
wherein the focus/defocus coil groups and the second superconducting coil group are configured to form a first layer which faces the vacuum duct; and
the bending coil is configured to form a second layer stacked on the first layer.

4. The particle-beam control electromagnet according to claim 1, wherein the second superconducting coil group includes:
a first correction coil configured to form a first correction magnetic field in a direction orthogonal to a traveling direction of the particle beam; and
a second correction coil configured to form a second correction magnetic field, which is orthogonal to the traveling direction of the particle beam and a direction of the first correction magnetic field.

5. The particle-beam control electromagnet according to claim 4, wherein the first correction coil and the second correction coil are arranged to be coaxially stacked.

6. An irradiation treatment apparatus comprising:
the particle-beam control electromagnet according to claim 1;
a rotating gantry configured to support the control electromagnet, rotate about a central axis, and irradiate the particle beam in a direction orthogonal to the central axis; and
a bed configured to perform moving and positioning of a patient placed thereon with respect to the particle beam to be irradiated.

7. The irradiation treatment apparatus according to claim 6, wherein the particle-beam control electromagnets are placed to be the trajectory of the particle beam orthogonal to the central axis.

* * * * *